(12) United States Patent
Peyman

(10) Patent No.: US 7,341,599 B1
(45) Date of Patent: Mar. 11, 2008

(54) INTRAOCULAR LENS FOR CORRECTING PRESBYOPIA

(75) Inventor: Gholam A. Peyman, New Orleans, LA (US)

(73) Assignee: Minu, LLC, Pittsboro, NC (US)

( * ) Notice: Subject to any disclaimer, the term of this patent is extended or adjusted under 35 U.S.C. 154(b) by 6 days.

(21) Appl. No.: 10/436,234

(22) Filed: May 13, 2003

Related U.S. Application Data (60) Provisional application No. 60/461,194, filed on Apr. 9, 2003.

(51) Int. Cl.
*A61F 2/16* (2006.01)

(52) U.S. Cl. .................................... 623/6.28

(58) Field of Classification Search ............... 623/4.1, 623/6.11, 6.14, 6.27, 6.28, 6.3, 6.31, 6.34–6.36, 623/6.38, 6.43
See application file for complete search history.

(56) References Cited

U.S. PATENT DOCUMENTS

| | | | |
|---|---|---|---|
| 4,581,031 A | 4/1986 | Koziol et al. | |
| 4,655,774 A | 4/1987 | Choyce | |
| 4,666,446 A | 5/1987 | Koziol et al. | |
| 4,840,175 A | 6/1989 | Peyman | |
| 4,932,971 A | 6/1990 | Kelman | |
| 4,994,080 A * | 2/1991 | Shepard ..................... | 623/6.64 |
| 5,098,444 A | 3/1992 | Feaster | |
| 5,358,520 A | 10/1994 | Patel | |
| 5,366,502 A | 11/1994 | Patel | |
| 5,405,384 A | 4/1995 | Silvestrini | |
| 5,443,507 A * | 8/1995 | Jacobi ..................... | 623/6.3 |
| 5,507,806 A * | 4/1996 | Blake ..................... | 623/6.33 |
| 5,628,797 A * | 5/1997 | Richer ..................... | 623/6.2 |
| 6,197,057 B1 | 3/2001 | Peyman et al. | |
| 6,277,146 B1 | 8/2001 | Peyman et al. | |
| 6,280,471 B1 | 8/2001 | Peyman et al. | |
| 6,436,092 B1 | 8/2002 | Peyman | |
| 6,554,424 B1 | 4/2003 | Miller et al. | |
| 2002/0103537 A1* | 8/2002 | Willis et al. ............... | 623/6.43 |
| 2003/0142268 A1 | 7/2003 | Miller et al. | |

FOREIGN PATENT DOCUMENTS

WO     WO 94/07435     4/1994

* cited by examiner

*Primary Examiner*—William H. Matthews
(74) *Attorney, Agent, or Firm*—Bell, Boyd & Lloyd LLP (57) ABSTRACT

An intraocular lens for modifying the refractive abilities of a natural lens or an existing artificial lens in an eye to correct for vision disorders such as presbyopia, myopia, hyperopia or astigmatism. Specifically, the lens system can be configured so that it does not effect far vision, while effecting near vision using a plus lens to correct for presbyopia. The lens system includes a lens portion and fastening members, with the lens portion being movably secured to at least one of the fastening members so that the position of the lens portion can be modified with respect to the optical axis, and the overall length of the lens system can be increased or decreased.

15 Claims, 10 Drawing Sheets

INTRAOCULAR LENS FOR CORRECTING PRESBYOPIA

This application claims benefit under 35 U.S.C. § 119(e) from U.S. Provisional Patent Application Ser. No. 60/461,194, filed on Apr. 9, 2003, the entire contents of which are incorporated herein by reference

CROSS-REFERENCE TO RELATED APPLICATIONS

This application is related to U.S. Pat. No. 6,197,057 to Peyman et al. entitled "LENS CONVERSION SYSTEM FOR TELEDIOPTIC OR DIFFRACTIVE CONFIGURATIONS", and copending U.S. patent application Ser. No. 10/356,730 entitled "SUBEPITHILIAL IMPLANT AND METHOD OF TREATMENT OF PRESBYOPIAN AND OTHER REFRACTIVE ERRORS", the entire contents of both of which are incorporated herein by reference.

BACKGROUND OF THE INVENTION

1. Field of the Invention

The present invention generally relates to a lens system for correcting vision in the eye. More specifically, the present invention generally relates to an intraocular lens system (IOL), which can be implanted in the anterior or posterior chambers of the eye in place of or in addition to the natural lens, or which can be implanted as piggyback IOL lens on the natural or artificial lens in the eye, for correcting presbyopia.

2. Description of the Related Art

A normal ametropic eye includes a cornea, lens and retina. The cornea and lens of the normal eye cooperatively focus light entering the eye from a far point, i.e., infinity, onto the retina. However, an eye can have a disease known as macular degeneration which can greatly degrade vision.

Macular degeneration has become one of the leading causes of blindness in adults. This disease affects the central retinal area known as the macula, which receives light focused by the cornea and lens and acute vision. Macular degeneration can lead to a gradual or sudden loss of vision to the level of 20/200 or less. Commonly, loss of vision only affects the central retinal area of about 0.25 to 4 square millimeters, and does not usually progress beyond this area, thereby leaving 95-99% of the retina unaffected. Thus, reading and driving vision can be lost, while peripheral vision remains intact.

U.S. Pat. Nos. 4,666,446 and 4,581,031, both to Koziol and Peyman, and both of which are incorporated by reference herein, each disclose intraocular lenses which are implanted in the eye in place of the natural lens to redirect the rays of light to minimize the adverse affect on vision caused by the macular degeneration of the eye. For example, U.S. Pat. No. 4,666,446 discloses an intraocular lens comprising a first portion including a diverging lens and a second portion including a converging lens. The converging lens provides the eye with substantially the same focusing ability of the natural lens prior to implantation of the intraocular lens. Thus, the eye will have decreased visual acuity due to the macular degeneration, but will also have unrestricted peripheral vision. The diverging lens, on the other hand, when combined with a converging lens positioned outside of the eye (e.g., a spectacle lens), provides a magnified image with increased visual acuity but a restricted visual field. Therefore, this type of intraocular lens creates a teledioptic lens system, which provides the patient with the choice of unmagnified but peripherally unrestricted vision or magnified but peripherally restricted vision.

U.S. Pat. No. 4,581,031 discloses an intraocular lens including a convex portion and a prismatic portion. The combined convex/prismatic lens directs rays of light away from the center of the retina that has been damaged by macular degeneration, and focuses those rays onto an undiseased area of the retina, thus providing greater visual acuity.

As discussed above, U.S. Pat. Nos. 4,666,446 and 4,581,031 clearly disclose that it is known to use particular types of intraocular lenses in place of the natural lens to reduce the adverse affect of macular degeneration on vision.

U.S. Pat. Nos. 5,098,444, 5,366,502, 5,358,520, and 4,932,971, as well as world patent application WO 94/07435, the entire contents of these documents being incorporated by reference herein, each disclose that it is known to attach a supplemental intraocular lens to an existing artificial intraocular lens to correct for ongoing degradation of vision. That is, if the ability of the eye to focus grows worse over time, instead of replacing the entire intraocular lens with a new intraocular lens having a different refractive power, a supplemental intraocular lens can be attached to the existing intraocular lens. This technique is less invasive and hence, less traumatic to the eye.

U.S. Pat. No. 6,197,057, the entire contents of which are herein incorporated by reference, relates to a lens system that combines a high plus lens with a plus and minus intraocular lens (IOL), so that the lens system works in a manner similar to a Galilean telescope. Generally, as shown in FIGS. 1 and 2 of the '057 patent, the high plus lens is outside the eye (i.e., in glasses or spectacles, or in a contact lens) and the plus and minus lens is an IOL that replaces or works in conjunction with the natural lens of the patient.

Additionally, if desired, the plus and minus lens can have a high minus portion in the center of the eye, while the portions surrounding the minus portion have no or substantially no refractive power, that is, the surrounding portion can be flat or substantially flat.

The Peyman '057 patent also discloses a supplemental intraocular lens that can be attached to the natural lens or an existing artificial lens to make the lens adaptable to function as a teledioptic or diffractive prismatic lens of the type described above.

Presbyopia, which is blurred vision of close up objects, for example, objects positioned for reading, typically occurs due to aging of the eye. A conventional method for correcting the refractive error in a cornea is keratophakia, that is, implantation of a lens inside the cornea. Keratophakia uses an implant which is placed into the cornea approximately equidistant from the exterior and interior surfaces of the cornea. The procedure is usually done by first preparing a lens from corneal donor tissue or synthetic material using a cryo-lathe. The lens is implanted by removing a portion of the cornea with a device called a microkeratome, and the tissue is sutured back into place over the lens. However, problems can arise when microkeratomes are used for cutting the cornea. First, irregular keratectomies or perforations of the eye can result. Second, the recovery of vision can be rather prolonged.

Another surgical technique exists that uses a femtosecond laser to separate layers inside the stromal portion of the eye, at least two-thirds of the distance from the top surface of the cornea to the inside of the eye. An incision is made to access this area and a solid inlay is inserted to help correct myopia in the eye. By separating the layers in the bottom two-thirds of the stromal portion, it is difficult to access the separated area to insert the inlay and virtually impossible to change or modify the inlay without another extensive surgical procedure. This procedure requires making an incision which is parallel or substantially parallel to the visual axis and is limited in the lateral direction by a maximum size of 0.3 mm to encase a relatively rigid inlay that forces the tissue in the lateral direction.

Additional surgical techniques exist that use ultraviolet light and short wavelength lasers to modify the shape of the cornea. For example, excimer lasers, such as those described in U.S. Pat. No. 4,840,175 to Peyman, which is incorporated herein by reference, emit pulsed ultraviolet radiation that can be used to decompose or photoablate tissue in the live cornea so as to reshape the cornea.

Specifically, the Peyman '175 patent discloses the laser surgical technique known as laser in situ keratomycosis (LASIK). In this technique, a portion of the front of the live cornea can be cut away in the form of a flap having a thickness of about 160 microns. This cut portion is removed from the live cornea to expose an inner surface of the cornea. A laser beam is then directed onto the exposed inner surface to ablate a desired amount of the inner surface up to 150-180 microns deep. The cut portion is reattached over the ablated portion of the cornea and assumes a shape conforming to that of the ablated portion. Additionally, in the LASIK procedure, a femtosecond laser can be used to cut and separate the flap.

Other conventional methods that have been employed specifically to correct presbyopia have been unsuccessful. Some of those methods include using an excimer laser to ablate the peripheral part of the cornea, expanding the sclera behind the limbus area of the cornea, implanting a plus lens inside the corneal stroma, using a multifocal intraocular lens after removal of the cataractous lens, and using bifocal glasses and bifocal contact lenses.

However, because only certain amount of cornea can be ablated without the remaining cornea becoming unstable or experiencing outbulging (ectasia), this technique is not especially effective in correcting very high myopia. That is, a typical cornea is on average about 500 microns thick. The laser ablation technique requires that at least about 250 microns of the corneal stroma remain after the ablation is completed so that instability and outbulging do not occur. Also, these conventional implants, while correcting a refractive error of the patient, also distort the normal vision of the patient.

Additional methods for correcting the refractive error in the eye include inserting an implant in-between layers of the cornea. Generally, this is achieved using several different methods. The first method involves inserting a ring between layers of the cornea, as described in U.S. Pat. No. 5,405,384 to Silvestrini, the entire contents of which is incorporated herein by reference. Typically, a dissector is inserted in the cornea and forms a channel therein. Once it is removed, a ring is then inserted into the channel to alter the curvature of the cornea. In the second method, a flap can be created similarly to the LASIK procedure and a lens can be inserted under the flap, as described in U.S. Pat. No. 6,102,946 to Nigam, the entire contents of which is incorporated herein by reference. The third method involves forming a pocket using an instrument, and inserting an implant into the pocket, as described in U.S. Pat. No. 4,655,774 to Choyce, the entire contents of which is incorporated herein by reference.

However, with the above described techniques, a knife or other mechanical instrument is generally used to form the channel, flap or pocket. Use of these instruments may result in damage or imprecision in the cut or formation of the desired area in which the implant is placed. Additionally, these conventional techniques do not include determination and testing of an appropriate implant for correcting a refractive error of a particular patient.

Also, prior methods for the treatment of presbyopia have been unsuccessful. One prior method involved implantation of a disc shaped inlay or lens over the central visual axis of the cornea. The disc inlay had a high index of refraction to correct presbyopia and/or hyperopia. However, because the disc covered the center area around the visual axis, the patient's farsighted vision was blurred by the inlay. Another prior method involved a ring shaped inlay implanted around the visual axis. The ring inlay had a lower index of refraction or an index of refraction that is the same as the cornea and therefor corrected myopic refractive errors instead of hyperopic or presbyopic error.

Therefore, there exists a need for an IOL and improved method of correcting refractive error, particularly presbyopia, in the eye, that does not distort the normal vision of the eye, such as far sighted vision. Moreover, there exists a need for selecting the appropriate IOL for correcting the particular refractive error of the patient.

SUMMARY OF THE INVENTION

An object of the invention is to provide a supplemental intraocular lens for modifying the natural lens or an existing artificial lens in an eye to correct for presbyopia.

A further object of the present invention is to provide a lens system that does not effect far vision, while effecting near vision using a plus lens to correct for presbyopia.

Still yet a further object of the present invention is to provide a substantially ring shaped, doughnut shaped or substantially semi-ring shaped IOL that can correct near vision caused by presbyopia, while not effecting far vision.

Still a further object of the invention is to provide intraocular lenses of the types described above which further include fastening members which enable those intraocular lenses to be secured in the anterior or posterior chambers of the eye.

Still yet further object of the invention is to provide intraocular lenses of the type described above which are capable of being secured directly in front of the surface of the natural or existing artificial lens in the eye as a piggyback lens.

Other objects, advantages, and features of the present invention will become apparent to those skilled in the art from the following detailed description, which, taken in conjunction with the annexed drawings, discloses preferred embodiments of the invention.

BRIEF DESCRIPTION OF THE DRAWINGS

Referring to the drawings which form a part of this disclosure.

DETAILED DESCRIPTION OF THE PREFERRED EMBODIMENTS

Figure 1:
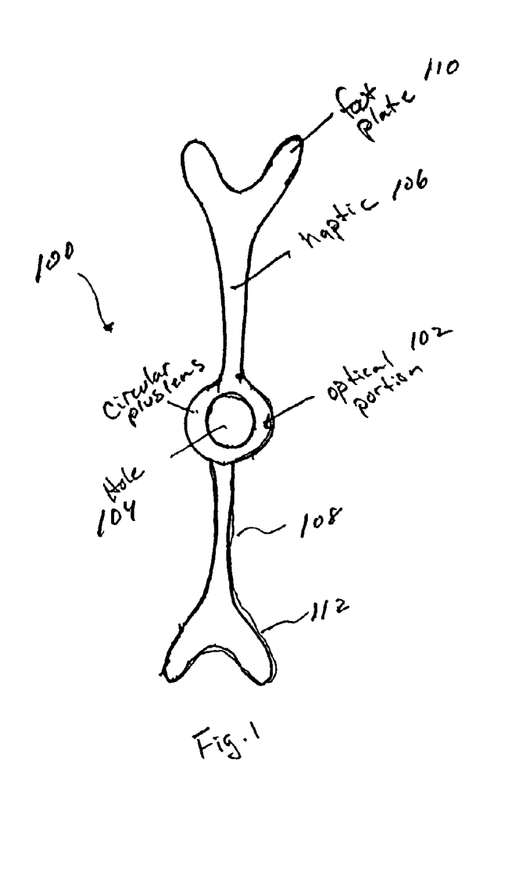
FIG. 1 illustrates an intraocular lens (IOL) according to an embodiment of the present invention.
Figure 2:
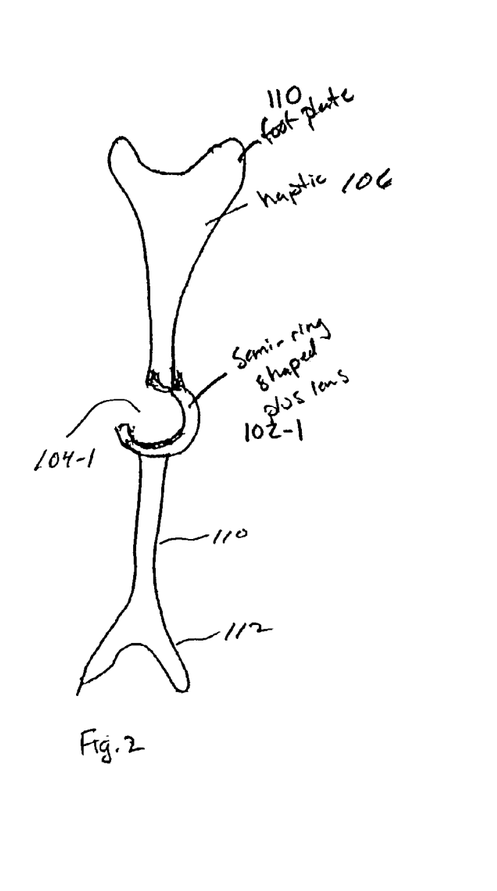
FIG. 2 illustrates an IOL according to another embodiment of the present invention.

As shown in FIGS. 1 and 2, a lens system 100 according to an embodiment of the present invention includes an optical portion 102 for use in correcting presbyopia. In this example, the optical portion 102 is preferably circular, substantially circular or doughnut-shaped to act as a plus lens, but can be any shape desired. For instance, as shown in FIG. 2, the optical portion 102-1 can be semi-circularly shaped or crescent shaped. The optical portion 102 includes an opening 104 that can be centered or substantially centered in the optical portion 102, or can be located anywhere in the optical portion 102 as appropriate. Similarly, the optical portion 102-1 can be shaped such that the opening 104-1 is centered with respect to the optical portion 102-1 or such that the opening 104-1 is off-centered by a desired distance.

The optical portion 102 (102-1), which can also be referred to as a lens, is preferably made of synthetic material, organic material, or a combination of both synthetic and organic material. Additionally, the lens can be formed from any suitable material. For example the lens can be formed from collagen, copolymer collagen, polyethylene oxide, polypropylene, polyproledine or hydrogel, or cross-linked organic material such as collagen, hyaluronic acid, mucopolysacoharide, glycoprotein, polymethylmethacrylate or silicone, to name a few, or a combination thereof. Further details of types of lens materials and structures are described in U.S. patent application of Gholam A. Peyman, entitled "ADJUSTABLE INLAY WITH MULTIZONE POLYMER-IZATION", Ser. No. 10/272,402, filed Oct. 17, 2002, the entire contents of which are herein incorporated by reference.

It is noted that although this embodiment of the present invention includes a plus lens for the correction of presbyopia, the lens can be configured in any manner desired. For example, the lens can be a minus lens for correcting vision that is adversely affected by macular degeneration, or can have alternative shapes such as touric and the like for correcting astigmatism, or can be shaped and have suitable power and refractivity to correct for hyperopia, myopia and the like.

As further shown in FIGS. 1 and 2, the lens systems 100 includes haptics 106 and 108 have foot plates 110 and 112, respectively, for mounting the lens systems 100 in the eye 116. The diameter of the hole 104 in the lens 102 is preferably between about 0.5 mm to about 5 mm, but can have any suitable size. It is also noted that it is not necessary to have a hole 104 or opening in the lens 102. For example, the hole 104 or opening can be replaced with a thin transparent portion that does not alter the path of light therethrough. In other words, the thin transparent portion can be nonrefractive or substantially nonrefractive. The thickness of the lens 102 is preferably within the range of at or about 0.025 mm to at or about 3 mm, and more preferably about 0.07 mm. However, the lens 102 can have any other suitable thickness. The diameter of the lens 102 is preferably within the range of at or about 0.5 mm to at or about 6 mm, but can be any suitable diameter.

Figure 3:
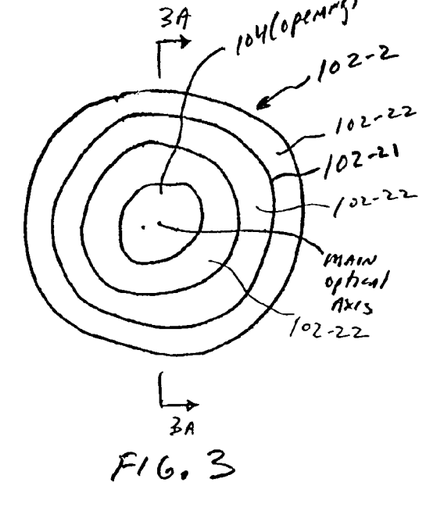
FIGS. 3 and 3A show front and cross-sectional views, respectively, of a lens portion for an IOL such as that shown in FIG. 1, that has diphractive optics to achieve a change in refractive power.
Figure 3A:
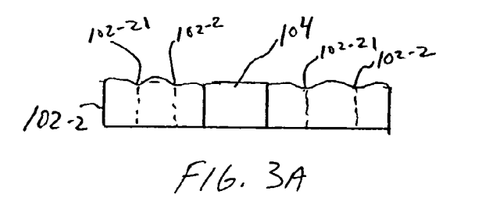

In addition, the lens 102 (lens 102-1) is preferably curved (instead of flat) and has the center portion thicker than the edges. However, if desired, the edges can be thicker than the center. It is noted that the lens can have any shape that would improve the vision in the eye of a particular patient. Furthermore, as shown in FIGS. 3 and 3A, the lens 102 can be configured as a diphractive lens 102-2, if desired. For example, the lens can have grooves 102-21 at different diameters along the surface thereof. These grooves, along with the multiple zones 102-22 separated by the grooves, act as prisms in the diphractive technology discussed above. Specifically, the multiple zones 102-22 can be recessed, or bumps, and have different refractive powers, such as +3 diopeters, +6 diopters, or any other suitable power which can enable the lens to correct for hyperopia, myopia, presbyopia, or astigmatism.

Figure 4:
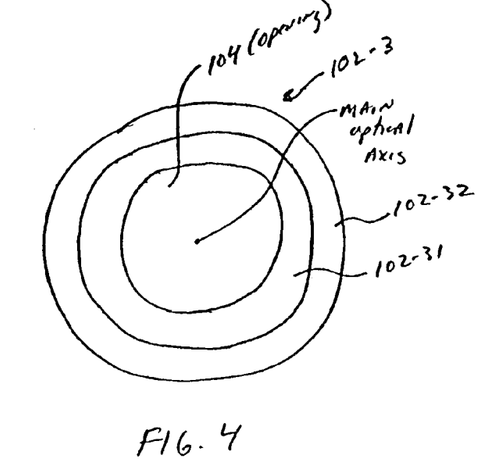
FIG. 4 shows a further configuration of a lens portion for the IOL of FIG. 1, wherein the lens portion is substantially ring-shaped and has a first portion, and a second portion with an edge that creates a gradual change in the refractive properties thereof.
Figure 5:
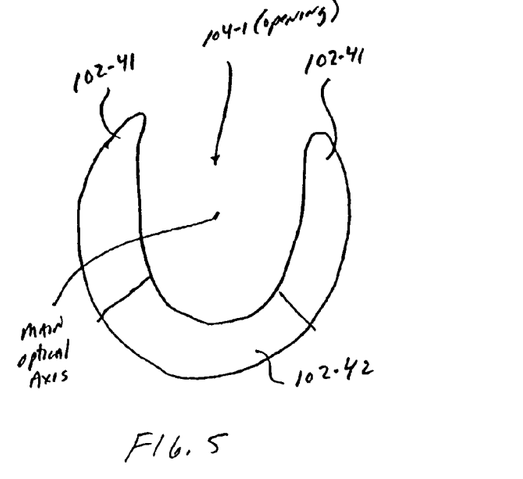
FIG. 5 shows a lens similar to the lens in FIG. 2, with an edge that creates a gradual change in the refractive properties thereof.

As shown in FIGS. 4 and 5, the edges of the lens portion can be configured to effect a gradual change in the refractive power thereof. For example, as shown in FIG. 4, the lens 102 can be configured as lens 102-3 having a first portion 102-31 that can have little or no refractive power, and a second portion 102-32 that has a varying thickness or shape so that its refractive power gradually changes. As shown in FIG. 5, the semicircularly shaped lens 102-1 shown in FIG. 2 can be configured as lens 102-4 having first portions 102-41 that can have little or no refractive power, and a second portion 102-42 that has a varying thickness or shape so that its refractive power gradually changes. For a further discussion of this type of configuration, see copending U.S. application Ser. No. 10/356,730 entitled "SUBEPITHILIAL IMPLANT AND METHOD OF TREATMENT OF PRESBYOPIAN AND OTHER REFRACTIVE ERRORS", the entire contents of which are incorporated herein by reference.

Figure 6:
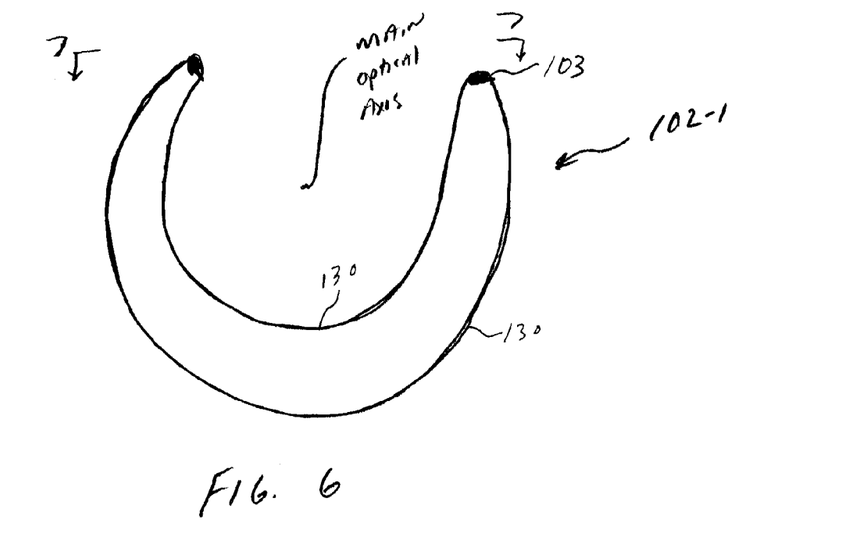
FIG. 6 shows the presbyopia lens portion of FIG. 2 relative to the main optical axis of the eye, and having glare-free material disposed thereon.
Figure 7:
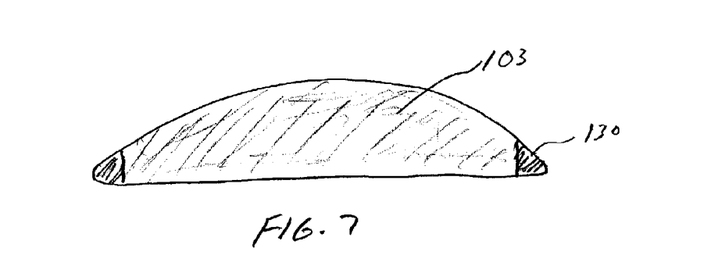
FIG. 7 shows the presbyopia lens portion of FIG. 6 taken along lines 7-7 of FIG. 6, with glare-free material disposed on the peripheral edges thereof.
Figure 8:
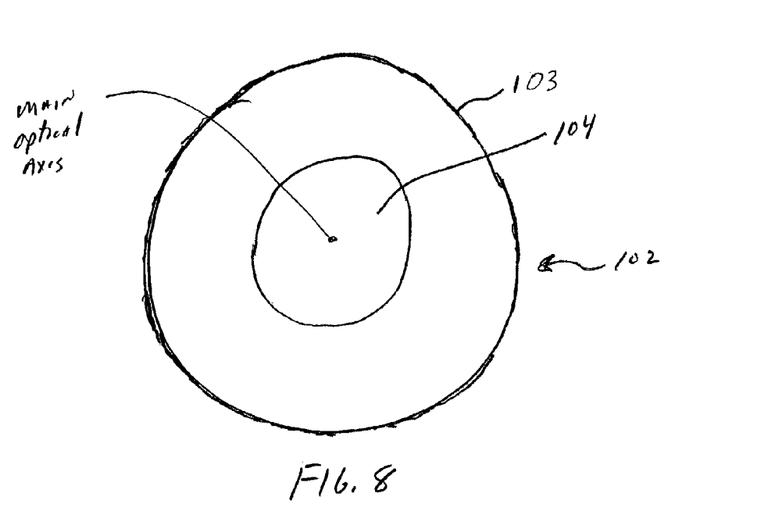
FIG. 8 shows the presbyopia lens portion of FIG. 1 relative to the main optical axis of the eye, and having glare-free material disposed thereon.

Furthermore, as shown in FIGS. 6-8, the edges of the lenses 102, 102-1 and all other lenses discussed above, as well as the haptics 106 and 108, can be pigmented or painted with a suitable light absorbing material 103 of a suitable color, such as black, to prevent light reflection and glare. A more detailed description of glare free IOLs is set forth in U.S. Pat. Nos. 6,277,146 and 6,280,471 both to Peyman et al., which are incorporated herein by reference.

Figure 9:
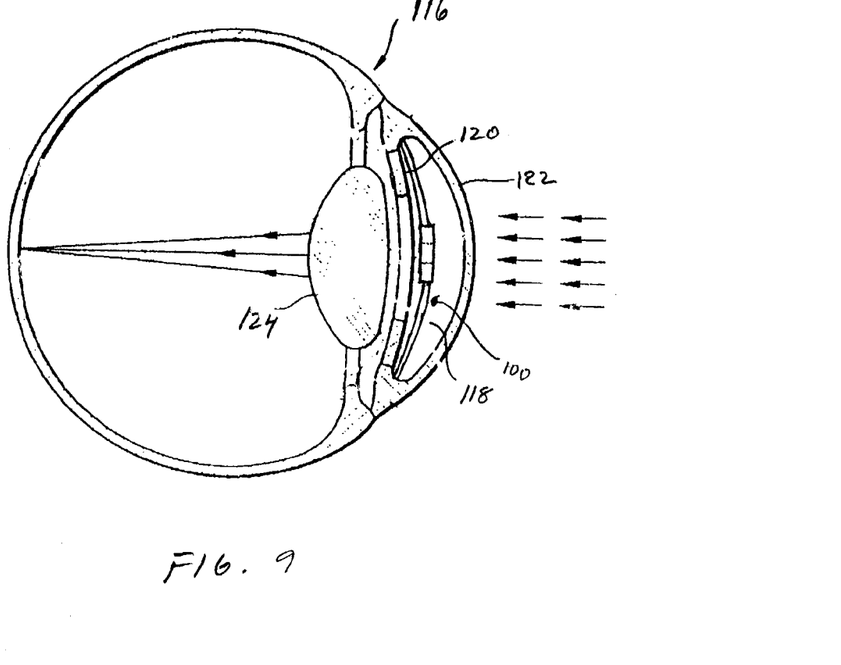
FIG. 9 shows the IOL of FIG. 1 implanted in the anterior chamber of the eye.
Figure 10:
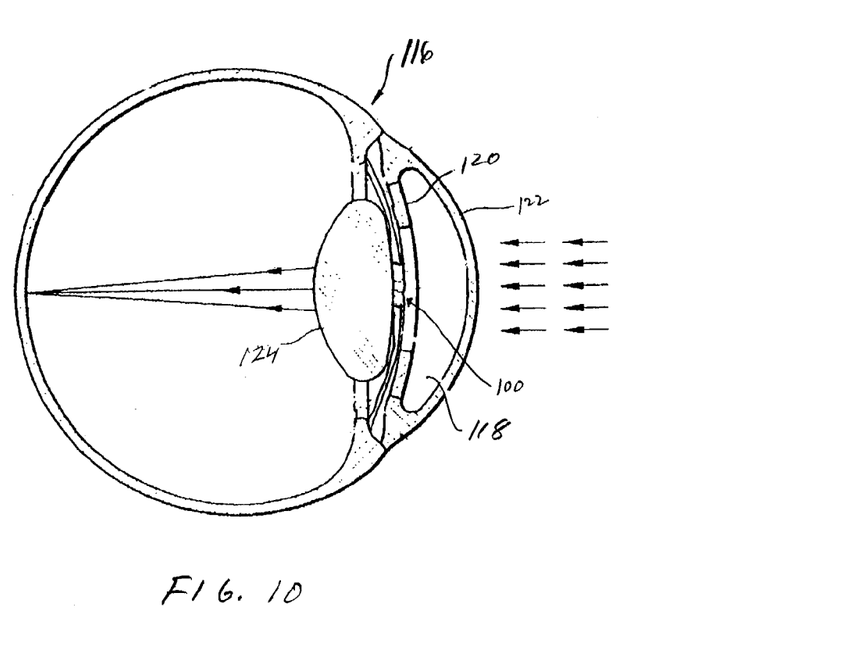
FIG. 10 shows the IOL of FIG. 1 implanted in the posterior chamber of the eye.
Figure 11:
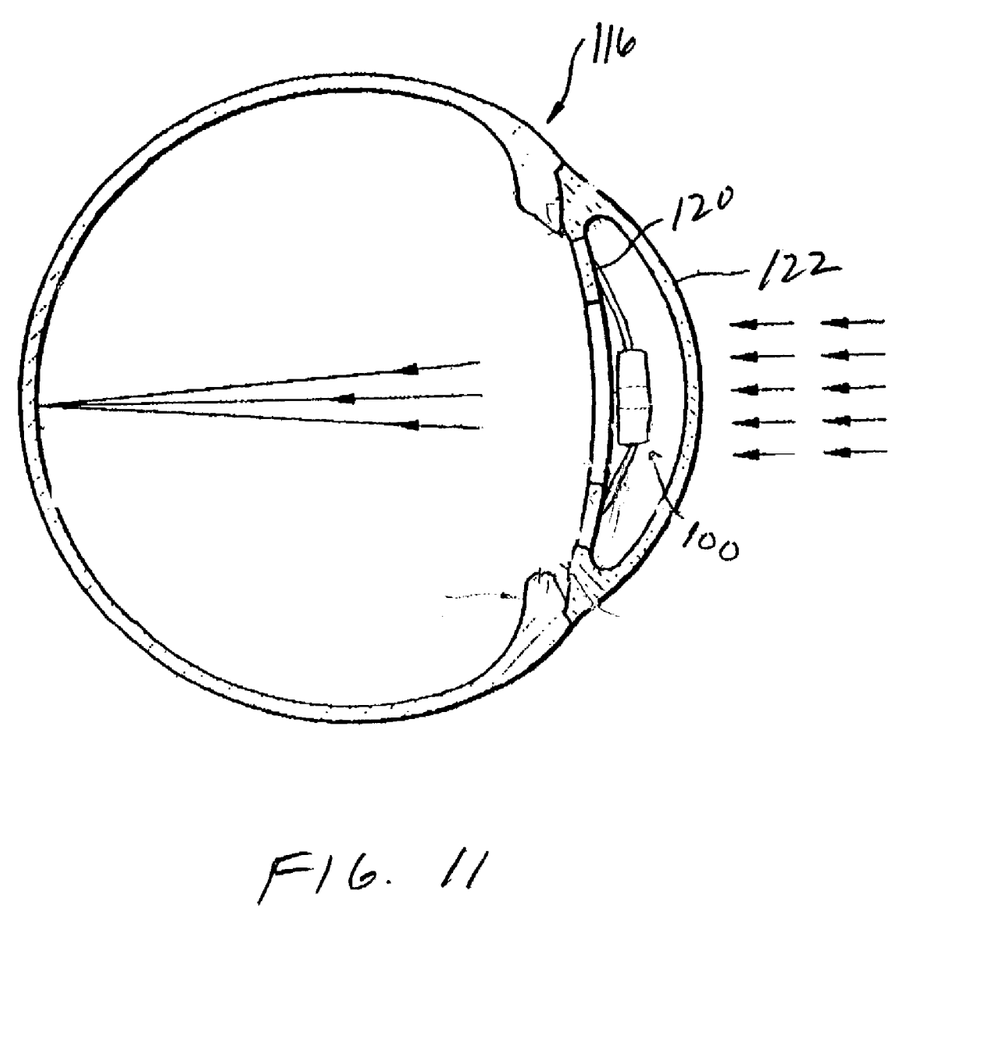
FIG. 11 shows an IOL of the type shown in FIG. 1 coupled to the iris.

As shown in FIG. 9, the lens system 100 can be positioned either in the anterior chamber 118 of the eye 116 in front of the iris 120 and behind the cornea 122. Alternatively, as shown in FIG. 10, the lens system 100 can be positioned in the posterior chamber 124 of the eye 116 behind the iris 120 and in front of the natural lens 124 or another artificial lens (not shown). Specifically, the lens system 100 can be positioned such that the lens 102 (102-1) is spaced from the front of the natural lens 124 (or artificial lens), or can be positioned in contact with the front of the natural lens 124 (or artificial lens) as a piggyback lens. Also, the lens system 100 can be implanted in place of the natural lens 124 of the eye 116 as shown in FIG. 11. The lens is coupled to the interior portion of the eye using haptics having a footplate or with any type of haptics or in any manner desired. For a further discussion of acceptable haptics, see U.S. Pat. Nos. 6,277,146 and 6,280,471 discussed above. As shown in FIGS. 3-6 and 8-11, the lens 102 (and all the variations discussed above) is positioned with the radial center of the lens 102 positioned to coincide with the main optical axis of the eye 116. The positioning allows the center portion to be used for far vision and the outer lens portion to be used for near vision, such as reading. Since there is no refractive portion in the center, there is no correction for far vision, while the outer portion of the lens corrects for presbyopia or any other vision problems desired.

Additionally, the lens shape and size can be altered (i.e., the lens can increase in size and/or volume or decrease in size and/or volume when exposed to the appropriate energy or altered in a desired manner) as described in U.S. patent application of Gholam A. Peyman entitled "A METHOD AND APPARATUS FOR CORRECTING THE REFRACTION OF AN INTRAOCULAR LENS AFTER IMPLANTATION IN THE EYE", Ser. No. 10/197,885, filed Jul. 19, 2002, and U.S. Pat. No. 6,436,092 to Gholam A. Peyman ENTITLED "ADJUSTABLE UNIVERSAL IMPLANT BLANK FOR MODIFYING CORNEAL CURVATURE AND METHODS OF MODIFYING CORNEAL CURVATURE THEREWITH", the entire contents of both of which are herein incorporated by reference.

Another embodiment of a lens system 200 for correcting presbyopia is shown in FIGS. 12-15. Specifically, lens system 200 includes an optical portion 202 that can be preferably ring or doughnut shaped and has an opening 204 therein. However, the lens 202 can have any desired shape and the features of lenses 102, 102-1 and their variations discussed above, and can be made of any of the materials discussed above. The lens 202 can have no refractive power or any degree of refractive depending on the application in which it is used. The lens can also have diphractive optical characteristics, and thus can be made very thin. Furthermore, the lens 202 can be adjustable by light as described in U.S. Pat. No. 6,436,092 to Peyman, the entire contents of which are incorporated herein by reference. In addition, as discussed above and is shown in FIGS. 9-11, the lens can be a piggy-back type lens, or can be placed in the anterior chamber of the eye 116, or in the posterior chamber of the eye 116 along with or in place of the natural lens 124 or another artificial lens in the eye 116.

Figure 12:
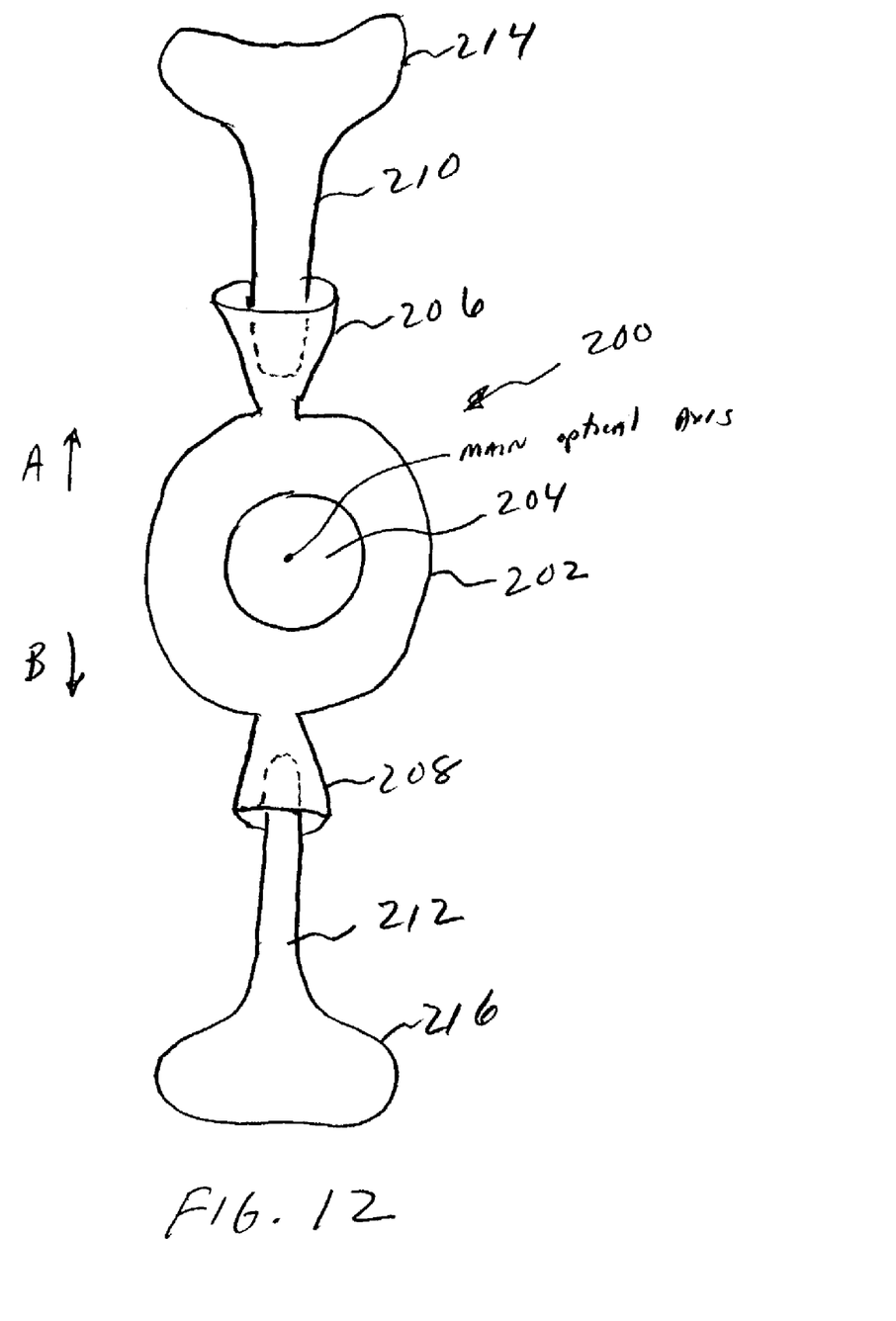
FIG. 12 illustrates another embodiment of an IOL lens system for correcting presbyopia, which includes a lens portion that is movable with respect to the haptics.

As will now be further described, the lens system 200 can be made adjustable so that the hole 204 in the center of the lens 202 can be increased or decreased in size. Specifically, as shown in FIG. 12, the lens 202 has a tube arrangement 206 and 208 that can receive the ends of haptics 210 and 212, respectively. Similar to haptics 106 and 108 discussed above, haptics 210 and 212 have foot plates 214 and 216, respectively. As indicated, the ends of the haptics 210 and 212 can be received in the tube arrangements 206 and 208 or the pulled out of the tube arrangements 206 or 208 to increase the overall lens of the lens system 200. Furthermore, in order to adjust the position of the opening 204 with regard to the optical axis of the eye 116, the lens 202 can be moved in a upward direction along arrow A so that the end of haptics 210 is received into tube arrangement 206 while the end of haptics 212 is moved in a direction out of tube arrangement 208. Likewise, the lens 202 can be moved down in a direction along arrow B so that the end of haptic 212 is further received into tube arrangement 208 while allowing the end of haptic 210 to move in the direction out of tube arrangement 206. This movement can be effected by inserting a small surgical tool into an opening in the eye 116, and then using the tool to move the haptics 210 and 212 as appropriate. Furthermore, an adhesive can be used, if desired, to more permanently attach the haptics 210 and 212 to the lens 202 once the lens has been positioned as appropriate and the desired overall length of the lens system 200 has been established.

Figure 13:
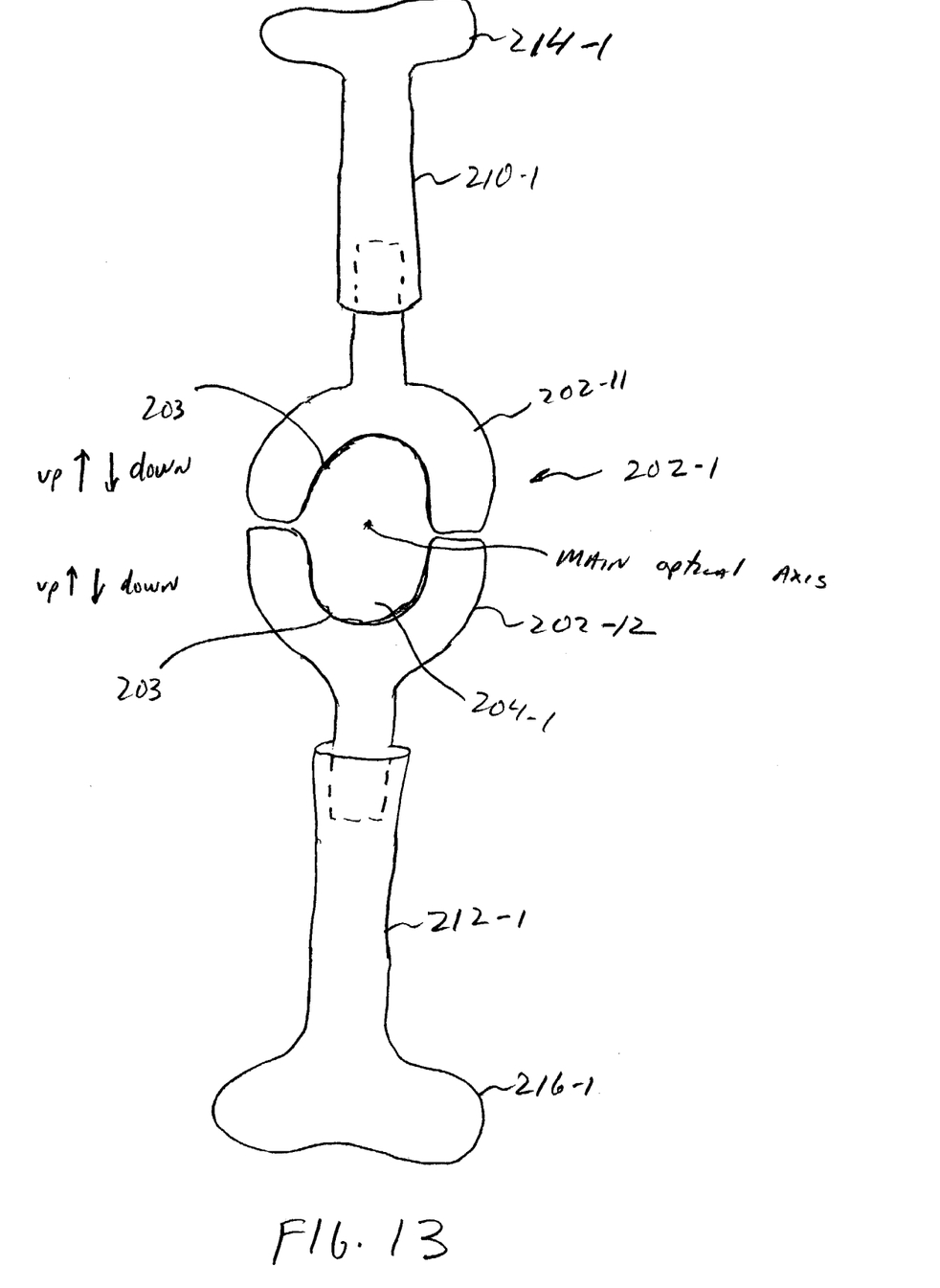
FIG. 13 illustrates a further embodiment of an IOL lens system for correcting presbyopia, which includes a sectional lens portion that is movable with respect to the haptics.
Figure 14:
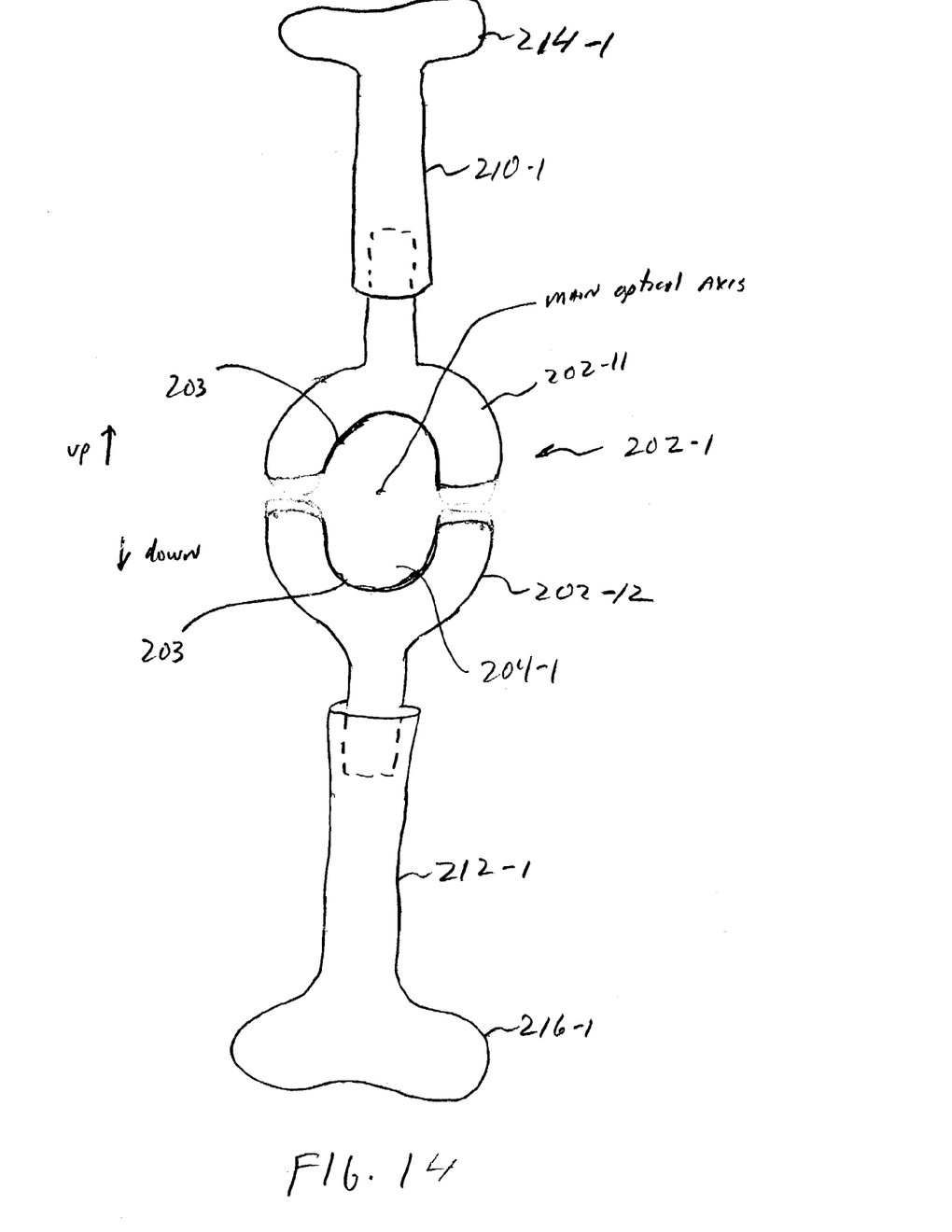
FIG. 14 illustrates the IOL lens system shown in FIG. 13 in which the lens portions have been moved to increase the opening in the lens.
Figure 15:
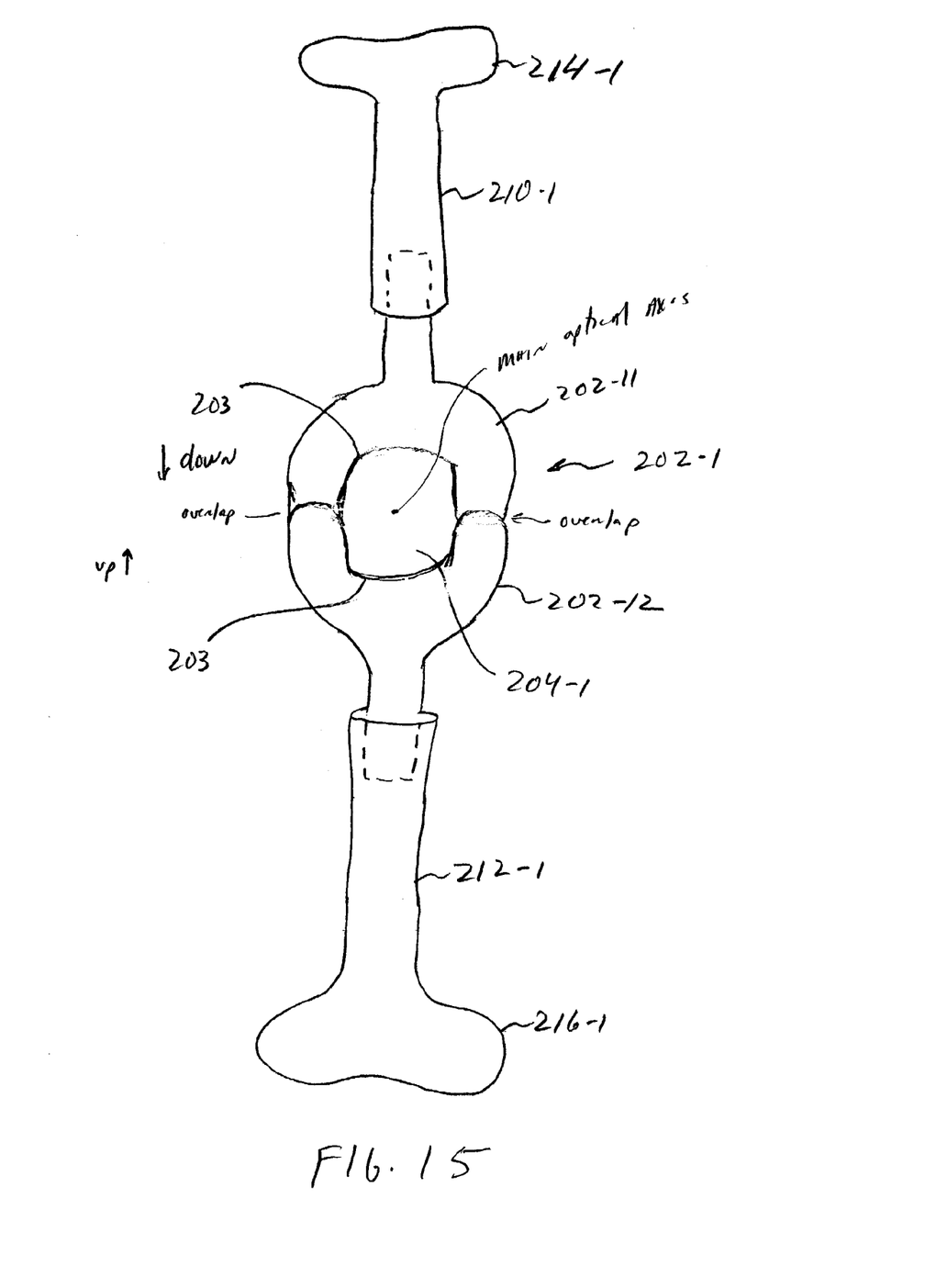
FIG. 15 illustrates the IOL lens system shown in FIG. 13 in which the lens portions have been moved to decrease the opening in the lens.

As further shown in FIGS. 13-15 specifically, the lens 202 can be configured as lens 202-1 which includes a top portion 202-11 and a bottom portion 202-12. As indicated, the lens 202-1 (as well as lens 202 shown in FIG. 12) can have a glare-free material 203 on its edges, such as pigmented edge or any of the glare free materials discussed above. Accordingly, by moving the top portion 202-11 and bottom portion 202-12 up or down with respect to the haptics 210-1 and 212-1 as shown in FIG. 14, the portions 202-11 and 202-12 of the lens 202-1 can be moved away from each other and therefore increase the size of opening 204-1. This movement can be effected by inserting a small surgical tool into an opening in the eye 116, and then using the tool to move the portions 202-11 and 202-12 as appropriate. Alternatively, as shown in FIG. 15, the upper portion 202-11 and lower portion 202-12 can be moved closer to each other to make the opening 204-1 smaller. As further discussed above, the lens portions 202-11 and 202-12 can have no refractive properties or any refractive properties as discussed above.

Figure 16:
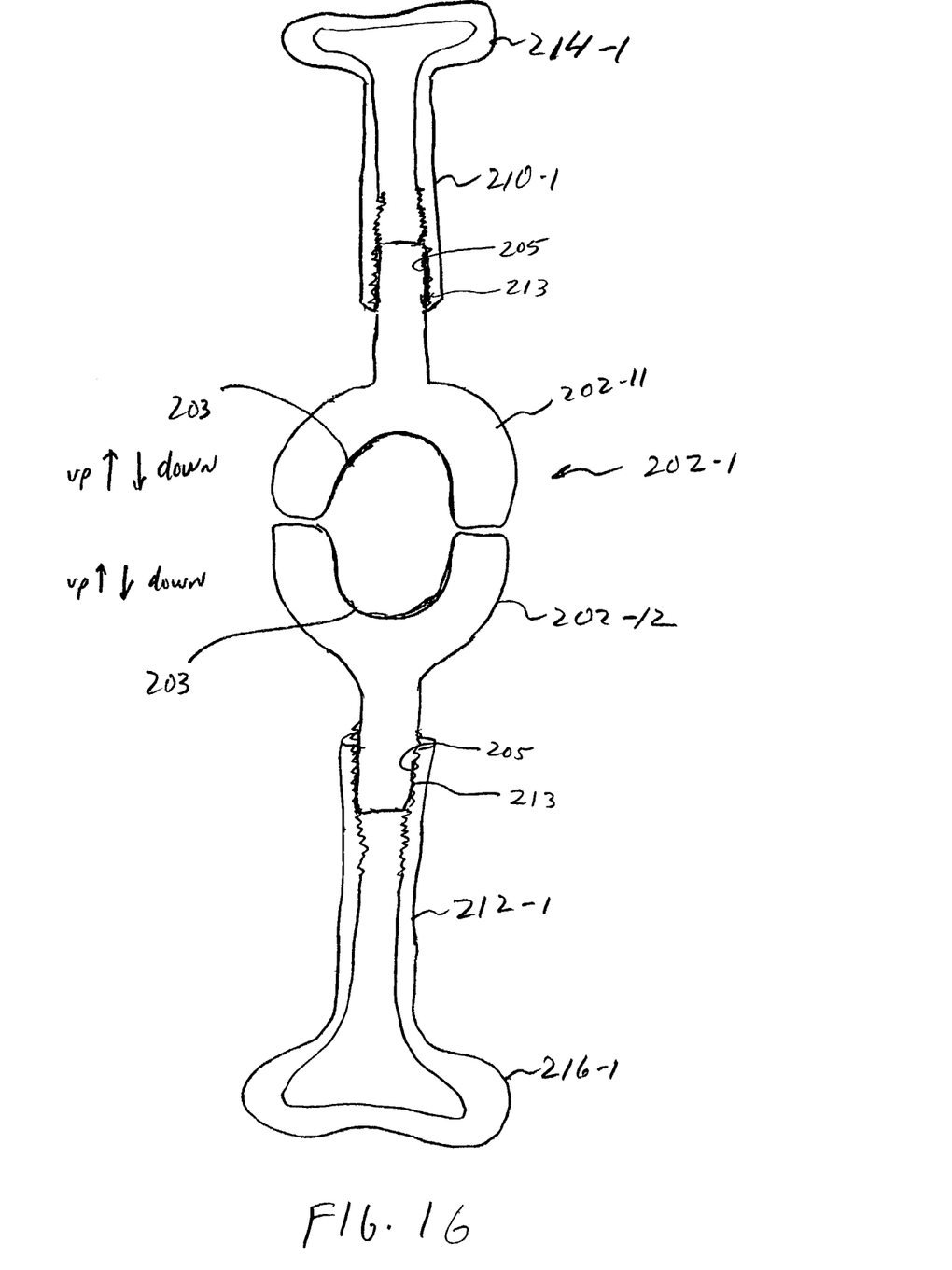
FIG. 16 illustrates variations to the haptics and lens of the lens system shown in FIG. 13.

In addition, as shown in FIG. 16, the haptics 210, 210-1, 212 and 212-1 and engaging portions of the lens 204 or 204-1 can have any particular configuration. For example, the haptics 210, 210-1, 212 and 212-1 need not be tube-shaped. Rather, they can be slotted, or the haptics and engaging portions of the lens 204 or 204-1 have a tongue and groove arrangements or any other type of arrangement that allows for mating and movement between the lens and the haptics. Furthermore, the anterior of the haptics 210, 210-1, 212 and 212-1 can have a serrated portion 213 which can mate with a serrated portion 205 of the engaging portions of the optic lens 204-1 so as to allow the mating portion to gradually mate with the haptics as shown in FIG. 16.

While certain embodiments have been chosen to illustrate the invention, it will be understood by those skilled in the art that various changes and modifications can be made therein without departing from the scope of the invention as defined in the appended claims.

What is claimed is:

1. An intraocular lens, adapted for implantation in an eye, comprising:
   a lens portion having a single refractive portion and a substantially nonrefractive portion, the substantially nonrefractive portion having a first surface, a second surface and a transparent substantially solid material extending from said first surface to said second surface, the nonrefractive portion being at least a central portion of the lens and allowing light to pass therethrough unaltered so that far vision is unaltered, the single refractive portion being substantially at the periphery of the lens portion and substantially surrounding said nonrefractive portion and configured to correct for near vision; and a plurality of haptics, adapted to couple said lens portion to an interior portion of the eye, such that said substantially nonrefractive portion is intersected by the optical axis of the eye.

2. An intraocular lens as claimed in claim 1, wherein:
said substantially nonrefractive portion is substantially round.

3. An intraocular lens as claimed in claim 1, wherein:
said haptics are adapted to couple said lens portion to the interior portion of the eye to position said lens portion in the anterior chamber of the eye.

4. An intraocular lens as claimed in claim 1, wherein:
said haptics are adapted to couple said lens portion to the interior portion of the eye to position the lens portion in the posterior chamber of the eye.

5. An intraocular lens as claimed in claim 1, wherein:
said haptics are adapted to couple said lens portion to an interior portion of the eye to enable said lens portion to contact the natural lens of the eye.

6. An intraocular lens as claimed in claim 1, wherein:
said haptics are adapted to couple said lens portion to an interior portion of the eye to enable said lens portion to contact an artificial lens implanted in the eye.

7. An intraocular lens as claimed in claim 1, wherein said lens is configured to correct for presbyopia.

8. An intraocular lens as claimed in claim 1, wherein said lens is configured to correct for myopia.

9. An intraocular lens as claimed in claim 1, wherein said lens is configured to correct for hyperopia.

10. An intraocular lens as claimed in claim 1, wherein said lens is configured to correct for astigmatism.

11. An intraocular lens as claimed in claim 1, wherein the distance between a first point on the border of the substantially nonrefractive portion and a second point on the border of the substantially nonrefractive portion is larger than three millimeters, the first point and second point being substantially coplanar on a plane that is substantially perpendicular to the optical axis.

12. An intraocular lens as claimed in claim 1, wherein said transparent substantially solid material does not alter the path of light therethrough when implanted in the eye.

13. An intraocular lens as claimed in claim 1, wherein the refractive portion has multiples zones with each zone having a different respective refractive power for near vision.

14. An intraocular lens as claimed in claim 1, wherein said single refractive portion is substantially continuous.

15. An intraocular lens, adapted for implantation in an eye, comprising:
a lens portion having a single refractive portion and a substantially nonrefractive portion, the substantially nonrefractive portion having a first surface, a second surface and a transparent substantially solid material extending from said first surface to said second surface, the nonrefractive portion being at least a central portion of the lens and allowing light to pass therethrough unaltered so that far vision is unaltered, the single refractive portion substantially surrounding said nonrefractive portion and being substantially continuous and configured to correct for near vision.

* * * * *